United States Patent [19]

Jindrich et al.

[11] Patent Number: 5,352,786
[45] Date of Patent: Oct. 4, 1994

[54] DI(2-PROPYL)ESTERS OF 1-FLUORO-2-PHOSPHONOMETHOXY-3-P-TO-LUENESULFONYLOXYPROPANES, THEIR PRODUCTION AND UTILIZATION

[75] Inventors: Jindrich Jindrich; Antonín Holy, Horní Pocernice, both of Czechoslovakia

[73] Assignee: Institute of Organic Chemistry and Biochemistry of the Academy of Sciences of the Czech Republic, Praha, Czechoslovakia

[21] Appl. No.: 969,852

[22] PCT Filed: May 19, 1992

[86] PCT No.: PCT/CS92/00013
 § 371 Date: Jan. 13, 1993
 § 102(e) Date: Jan. 13, 1993

[87] PCT Pub. No.: WO92/20691
 PCT Pub. Date: Nov. 26, 1992

[30] Foreign Application Priority Data

May 20, 1991 [CS] Czechoslovakia ............. PV 1475-91

[51] Int. Cl.[5] .................................. C07F 9/02
[52] U.S. Cl. .................................. 544/243; 544/244; 558/45; 558/44
[58] Field of Search ................... 558/45; 544/243, 244

[56] References Cited

U.S. PATENT DOCUMENTS 5,130,427 7/1992 Alexander et al. ................. 544/243

FOREIGN PATENT DOCUMENTS

0454427A1 10/1991 European Pat. Off. .

OTHER PUBLICATIONS

Balzarini et al, "9-[(2RS)-3-Fluoro-2-phosphonylmethoxypropyl] derivatives of purines: A class of highly selective antiretroviral agents *in vitro and in vivo*", *Proc. Natl. Acad. Sci. USA*, vol. 88, pp. 4961–4965, (Jun. 1991).
Balzarini et al, "5-Phosphoribosyl 1-Pyrophosphate Synthetase Converts the Acyclic Nucleoside Phosphonates 9-(3-Hydroxy-2-Phosphonylmethoxypropyl)Adenine and 9-(2-Phosphonylmethoxyethyl)-Adenine Directly to their Antivirally Active Diphosphate Derivatives", *The Journal of Biological Chemistry*, vol. 266, No. 14, pp. 8686–8689, (May 15, 1991).
Bronson et al, "Synthesis and Antiviral Activity of the Nucleotide Analogue (S)-1-[3-Hydroxy-2-(phosphonylmethoxy)propyl] cystosine", *J. Med. Chem.*, vol. 32, pp. 1457–1463, (1989).

*Primary Examiner*—José G. Dees
*Assistant Examiner*—Dwayne C. Jones
*Attorney, Agent, or Firm*—Max D. Hensley

[57] ABSTRACT

The invention relates to new compounds, di(2-propyl) esters of (R)-, (S)- and (RS)-1-fluoro-2-phosphonomethoxy-3-p-toluenesulfonyloxypropane and the method of producing them. The compounds can be used with advantage in the preparation of N-(3-fluoro-2-phosphonomethoxypropyl) derivatives of heterocyclic purine and pyrimidine bases that have antiviral activity.

7 Claims, No Drawings

DI(2-PROPYL)ESTERS OF 1-FLUORO-2-PHOSPHONOMETHOXY-3-P-TOLUENESULFONYLOXYPROPANES, THEIR PRODUCTION AND UTILIZATION

TECHNICAL FIELD

This invention relates to di(2-propyl) esters of 1-fluoro-2-phosphonomethoxy-3-p-toluenesulfonyloxypropanes, the method of their preparation and utilization in production of antivirals, N-(3-fluoro-2-phosphonomethoxypropyl) derivatives of heterocyclic purine and pyrimidine bases.

BACKGROUND ART

N-(3-Fluoro-2-phosphonomethoxypropyl) derivatives of heterocyclic purine and pyrimidine bases (FPMP-derivatives) occupy a significant place among compounds effective against retro-viruses causing serious illnesses in man and animals. Under in vitro conditions, these compounds exhibit biological parameters (selectivity of action) better than e.g. 9-(2-phosphonomethoxyethyl)adenine (R. Pauwels, J. Balzarini, D. Schols, M. Baba, J. Desmyter, I. Rosenberg, A. Holy, E. De Clercq: Antimicrob. Ag. Chemother. 32, 1025 (1988)). The said derivatives were hitherto accessible from N-(3-fluoro-2-hydroxypropyl) derivatives of purine or pyrimidine bases (prepared e.g. according to CS-patent application PV 2047-90) by reaction with dialkyl p-toluenesulfonyloxymethanesulfonates or methanesulfonyloxymethanephosphonates in the presence of sodium hydride and subsequent removal of the protecting groups by acid or alkaline hydrolysis and finally with bromotrimethylsilane. The drawback of this method (according to CS-patent application PV 2047-90) is that it is necessary first to prepare the optically active N-(3-fluoro-2hydroxypropyl) derivatives and perform their multistage protection. Another possible solution would be condensation of the heterocyclic base (its silyl derivative or alkali metal salt) with a suitable optically active organophosphorus synthon that has a preformed structure of the side chain of FPMP derivatives. Such a reaction of suitably protected derivatives of glycerol with dialkyl esters of p-toluenesulfonyloxymethanephosphonic acid, followed by partial deblocking and introduction of the reactive tosyl or mesyl group has been utilized e.g. in producing analogous N-(3-hydroxy-2-phosphonomethoxypropyl) derivatives (J. J. Bronson, I. Ghazzouli, M. J. M. Hitchcock, R. R. Webb, J. C. Martin: J. Med. Chem. 32, 1457 (1989)). Still another approach made use of introduction of the esterified phosphonomethyl ether functionality on the hydroxyl component via an acetoxymethyl ether by treatment with bromotrimethylsilane and trialkyl phosphite (CS-patent application PV 3871-90).

DISCLOSURE OF INVENTION

The above-mentioned drawbacks in the so far used methods of preparing N-(3-fluoro-2-phosphonomethoxypropyl) derivatives of purine and pyrimidine bases are removed by this invention relating to di(2-propyl) esters of 1-fluoro-2-phosphonomethoxy-3-p-toluenesulfonyloxypropanes of the general formula I

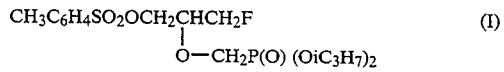

where the absolute configuration at carbon atom C2 is R, S or RS, and the method of preparing them which is characterized in that 1-fluoro-2,3-propanediols of the general formula II

where the absolute configuration at carbon atom C2 is R, S or RS, are reacted with p-toluenesulfonyl chloride in the presence of a tertiary amine, preferably triethylamine or pyridine, in an inert organic aprotic solvent, preferably benzene or dichloromethane, or only in pyridine, the obtained 1-fluoro-3-p-toluenesulfonyloxy-2-propanols of the general formula III

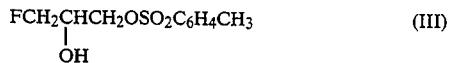

where the absolute configuration at carbon atom C2 is R, S or RS, are reacted with dimethoxymethane in the presence of phosphorus pentoxide in an inert organic solvent, preferably dichloromethane, the resulting 1-fluoro-2-methoxymethoxy-3-p-toluenesulfonyloxypropanes of the general formula IV

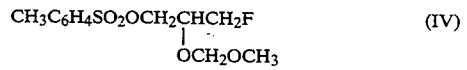

where the absolute configuration at carbon atom C2 is R, S or RS, are treated with acetic anhydride in the presence of a Lewis acid, preferably boron trifluoride etherate, at −5° to +5° C., the obtained 2-acetoxymethoxy-1-fluoro-3-p-toluenesulfonyloxypropanes of the formula V

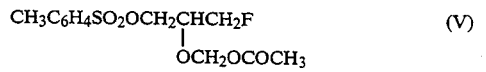

where the absolute configuration at carbon atom C2 is R, S or RS, are heated with bromotrimethylsilane to 100°–120° C. preferably in toluene, the volatile material is evaporated in vacuo and the residue is heated with tri(2-propyl) phosphite at 100°–120° C., and the compounds of the general formula I are isolated, preferably by chromatography.

The invention also relates to the utilization of the said compounds of the formula I in the preparation of N-(3-fluoro-2-phosphonomethoxypropyl) derivatives of heterocyclic purine and pyrimidine bases of the general formula VI

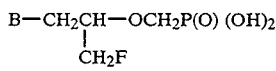

where the absolute configuration at carbon atom C2 is R, S or RS and B is a substituted purin-9-yl, purin-7-yl, pyrimidin-1-yl or pyrimidine-3-yl moiety or their aza or diaza analogues.

which is characterized in that compounds of the formula I are reacted with a sodium salt of the substituted purine or pyrimidine heterocyclic base, its aza or diaza analogue, or their acyl, preferably benzoyl, derivatives, or with a mixture of these bases with an alkali metal carbonate, preferably cesium carbonate, in dimethylformamide at 60°–140° C., whereupon the solvent is evaporated in vacuo and the residue is treated with sodium methoxide in methanol and then with bromotrimethylsilane in an inert organic solvent, preferably in acetonitrile and the resulting compounds of the general formula VI are isolated by chromatography, preferably on ion-exchanging resins.

Devising an organophosphorus synthon suitable for the preparation of FPMP-derivatives of the general formula VI involves the following problems: (a) the choice of a suitable reactive group capable of substituting the active form of the heterocyclic base, (b) the choice of suitable ester protecting groups on the phosphonic acid moiety, and (c) carrying out the whole synthetic sequence leading to the chiral synthon from an easily accessible chiral compound with preservation of optical purity of both the synthon and the final product.

The starting fluoro derivatives of the formula II are prepared e.g. by reaction of 1-O-p-toluenesulfonlglycerols with alkali metal fluorides; this reaction can be realized with the racemic compound (CS-patent application PV 2048-90) as well as with both the enantiomeric derivatives. In such case one can make use of p-toluenesulfonyl esters of 4-hydroxymethyl-2,2-dimethyl-1,3-dioxolanes of the formula VII

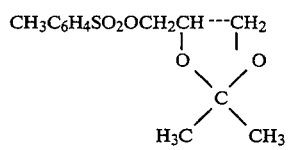

of which the (R)-enantiomer is readily accessible from D-mannitol (A. Holy: Collect. Czech, Chem. Commun. 40, 187 (1975)) whereas the (S)-antipode can be obtained e.g. from D-ribonolactone. Thus, e.g. a solution of 2,3-O-isopropylidene-5-O-(p-toluenesulfonyl)-D-ribonolactone (50 g) (L. Hough, J. K. N. Jones, D. L. Mitchel: Can. J. Chem. 36, 1720 (1958)) in dioxane (500 ml) stirred with concentrated hydrochloric acid (50 ml) at room temperature for 12 h. Then water (130 ml) is added and the mixture is neutralized by addition of solid sodium hydrogen carbonate. The bottom aqueous layer is separated, washed with ethyl acetate (500 ml), and the combined ethyl acetate and dioxane solutions are dried over magnesium sulfate. After filtration, the solvents are evaporated and the dry residue is crystallized by addition of toluene (500 ml) to its boiling solution in ethyl acetate (130 ml); yield 31.6 g (71%) of 5-O-(p-toluenesulfonyl)-D-ribonolactone. A solution of this compound (30.7 g) in a mixture of water (75 ml) and dioxane (75 ml) is cooled to 0° C. and a solution of sodium periodate (22.8 g) in water (165 ml) is added. The mixture is stirred at room temperature for 20 min, cooled to 0° C., and after 20 min dioxane (150 ml) is added. After filtration, sodium borohydride (4.73 g) added in portions to the filtrate, the temperature being kept below 20° C. After 0.5 h at room temperature, the reaction mixture is poured into ethyl acetate (1.3 liter) and shaken successively with 1HCl (saturated with sodium chloride) (2×150 ml) and a 1:1 mixture of saturated solutions of sodium chloride and sodium hydrogen carbonate (2×150 ml). The ethyl acetate solution is then dried over magnesium sulfate, filtered and the solvent is evaporated to dryness, yielding 20 g (80%) of (S)-3-O-(p-toluenesulfonyl)glycerol. A solution of this compound (27 g) in acetone (150 ml) is stirred with 2,2-dimethoxypropane (20.2 ml) and trifluoromethanesulfonic acid (10 µl) at room temperature. After standing overnight at ambient temperature, triethylamine (0.5 ml) is added, the reaction mixture is concentrated to a minimum volume, the residue is dissolved in toluene (500 ml), washed with water (3×250 ml) and dried over magnesium sulfate. The drying agent is filtered off and the filtrate is evaporated in vacuo to afford (S)-1,2-O-isopropylidene-3-O-(p-toluenesulfonyl)-glycerol (28.3 g).

Reaction of 1,2-isopropylidene-3-O-(p-toluenesulfonyl) glyceroyls with potassium fluoride in diethylene glycol affords fluoromethyl derivatives which can be converted into the starting compounds of the formula II (W. J. Lloyd, R. Harrison: Carbohyd. Res. 20, 133 (1971)). Thus, e.g., a mixture of (S)-1,2-O-isopropylidene-3-O-(p-toluenesulfonyl)glycerol (100 g), potassium fluoride (30 g) and diethylene glycol is heated to 160°–170° C. for 2 h under vigorous stirring and introduction of nitrogen. The product which distills is collected in a receiver cooled with dry ice; yield 21 g (45%) of (S)-1-deoxy-1-fluoro-2,3-O-isopropylideneglycerol. A mixture of this product and 1M HCl (50 ml) is stirred at room temperature for 10 h. Then it is neutralized with an anion-exchanging resin (HCO$_3^-$ form), filtered, and the resin is washed with methanol (50 ml). The combined filtrates are treated with charcoal and after filtration the solvent is evaporated and the product distilled in a vacuum of an oil pump at bath temperature not exceeding 140° C.; yield 12.4 g (84%) of (S)-3-fluoro-1,2-propanediol.

As follows from the previous studies, for the desired N-substitution of heterocyclic bases the presence of a reactive chloro, p-toluenesulfonyloxy or methanesulfonyloxy group in the synthon I represents an advantage. p-toluenesulfonyl derivatives are well accessible from alcohols can be easily purified. Therefore, the synthon I can be prepared preferably from 1-fluoro-3-p-toluenesulfonyloxy-2-propanol of the formula III, which can be easily obtained from compounds II by tosylation in pyridine or in inert organic sovents (benzene, chlorinated hydrocarbons) in the presence of a slight excess of a tertiary base (e.g. pyridine, triethylamine, di(2-propyl)ethylamine). The tosyl derivatives III are purified by chromatography on silica gel.

The introduction of the phosphonomethyl ether functionality on the carbon atom in position 2 in compound III makes use of 2-methoxymethyl ether IV as the key intermediate. This is easily prepared from compound III by acid-catalyzed transacetaxlization with dimethoxymethane in the presence of phosphorus pentoxide. The reaction is heterogeneous but the product is obtained in high yield by chromatography of the organic phase.

The methoxymethyl group in compound IV can be converted into the acetoxymethyl group by reaction with acetic anhydride in the presence of a Lewis acid, e.g., boron trifluoride etherate, and the obtained acetoxymethoxy derivative V is immediately converted into the reactive 2-bromomethyl ether by treatment with bromotrimethylsilane. This reaction proceeds sluggishly even at relatively high temperatures and it is advisable to follow its course by thin-layer chromatography. The solvent and acetoxytrimethyl-silane are evaporated in vacuo and the crude product is immediately reacted with trialkyl phosphite Tri (2-propyl)-phosphite appears to be reagent of choice: it is sufficiently reactive, the 2-bromopropane arising in the reaction is volatile and can be removed during the reaction, and the formed di(2-propyl) ester of phosphonic acid in the synthon I is not capable of alkylation of the heterocyclic base, unlike e.g. the corresponding ethyl, or particularly methyl, ester. However, synthons analogous to the compound I, containing other ester groups such as dimethyl, diethyl or di (2,2-dimethylpropyl) ester etc. can be prepared by the analogous reaction with the corresponding trialkyl phosphite. Synthon I containing a reactive chloro, p-toluenesulfonyloxy or methanesulfonyloxy group which is prepared from trialkyl phosphite will have formula VIII

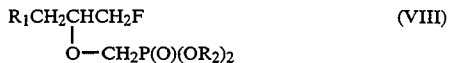

where $R_1$ is a reactive chloro, p-toluenesulfonyloxy or methanesulfonyloxy group, $R_2$ is alkyl, and the absolute configuration at carbon atom C2 is R, S or RS. Synthon I containing the reactive p-toluenesulfonyloxy group and which is prepared from trialkyl phosphite will have formula IX

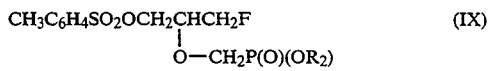

where $R_2$ is defined above and the absolute configuration at carbon atom C2 is R, S or RS. This react ion proceeds smoothly and after its end and evaporation of volatile products the desired product, synthon I, is obtained by chromatography on silica gel.

All stages of this reaction sequence are realized in high yields so that the final over yield from the starting compound II exceeds 40%. The reaction steps require no special materials or equipment and the optical purity of the end product I is determined only by the optical purity of the compound II. It follows from the optical purity of the known compounds of the formula IV that are ultimately prepared from the synthon I by condensation with sodium salts of heterocyclic bases.

Such reaction takes place in dimethylformamide with a suspension of tile sodium salt obtained e.g. by in situ reaction of the base with an equimolar amount of sodium hydride. An equimolar amount of compound I is used i n the reaction which is carried out at 80°–100° C. under exclusion of air moisture. Another particularly advantageous modification of this method consists in heating compound I with the heterocyclic base in the presence of cesium carbonate which proceeds substantially faster and under formation of less side-products.

With purine derivatives of the formula VI, which are of particular interest because of their antiretroviral activity, such alkylation with sodium salts of some bases (e.g. adenine, 2,6-diaminopurine, 6-methylthiopurine, 3-deazaadenine) takes place invariably in the N9-position, with other bases (hypoxanthine) in position N7; with some other bases (e.g. guanine, 2-aminopurine, 1-deazaadenine) a mixture of the N9- and N7-isomers is formed. In such cases it is advantageous to use indirect methods based on subsequent conversion of the heterocyclic base in compounds of the general formula VI or their precursors modified at the base. Such is the case e.g. in the preparation of the hypoxanthine or xanthine derivative by deamination of compound, containing adenine or guanine, with nitrous acid or its esters, or in the synthesis of the 2-hydroxyadenine derivative by specific deamination of compound derived from 2,6-diaminopurine. The guanin-9-yl derivative as well as its N7-isomer are prepared by hydrolysis of compound obtained from 2-amino-6-chloropurine. The same intermediate can be used to prepare 2-amino-6-substituted derivatives. Thus, compound of the formula VI containing 2,6-diaminopurine is obtained by hydrogenation of the corresponding 2-amino-6-azidopurine compound.

The reaction of compounds I can also be performed with pyrimidine derivatives; in such alkylations it is most important to ensure the regiospecific course of the reaction in position N1: this is preferably achieved using 4-alkoxy-2-pyrimidones. The obtained N1-substituted derivatives may be then converted by an acid hydrolysis with aqueous mineral acid or e.g. dilute acetic acid uracil or thymine derivatives or, alternatively, by aminolysis, e.g. with alcoholic solutions of ammonia, primary or secondary amines at elevated temperatures to the derivatives of cytosine, 5-methylcytosine or their N-substituted analogs.

The intermediate obtained by condensation of compound I with the base is either isolated by chromatography and is further processed as described below or the reaction mixture is directly methanolyzed (which removes the N-acyl group from the heterocyclic base). In the latter case, the obtained mixture is deionized, e.g. on a column of cation-exchanging resin (such as Dowex 50) in H+-form, and the di(2-propyl)ester of compound VI is isolated; this compound is sufficiently stable to withstand e.g. elution with dilute (1:10) aqueous ammonia from the resin. After drying, the ester groups in this intermediate are removed by reaction with bromotrimethylsilane, e.g. in acetonitrile. After evaporation of the solvent, hydrolysis of the residue and desalting, the pure product of the formula VI is isolated by chromatography on an ion-exchanger or chromatography on hydrophobized silica gel.

The optical purity of the thus-prepared compounds of the formula VI is proved e.g. by HPLC in 4 mM copper(II) sulfate and 4 mM L-phenylalanine at pH 3.1. The above-described procedure ffords compounds VI of optical purity >95%.

The invention is further illustrated by examples of execution without being in any way limited.

EXAMPLES OF EXECUTION

Example 1

A solution of p-toluenesulfonyl chloride (26.4 g, 138 mmol) in pyridine (30 ml) is added −30° C. to a solution of (S)-1-fluoro-2,3-propanediol (12.4 g, 132 mmol) in pyridine (30 ml). After standing at −30° C. for 48 h, the reaction mixture is poured into ethyl acetate (1300 ml) and under ice-cooling shaken with 1M HCl to acid reaction of the aqueous layer, then with water, sodium hydrogen carbonate solution and again with water. After drying over magnesium sulfate and filtration, the solvent is evaporated in vacuo and the residue is chromatographed on silica gel (500 g) in toluene and then in a 50:1 mixture of toluene and ethyl acetate. Yield 21 g (64%) of (S)-1-fluoro-3-(p-toluenesulfonyloxy)-2-propanol. For $C_{10}H_{13}FO_4S$ (248.3) calculated: 48.37% C, 5.27% H, 7.65% F, 12.91% S; found: 48.54% C, 5.31% H, 7.43% F, 12.80% S.

Phosphorus pentoxide is added at room temperature to a stirred mixture of this compound (11 g, 44.3 mmol), dimethoxymethane (11 ml) and dichloromethane (11 ml) until the starting compound disappears to afford the desired product (monitored by TLC in toluene-ethyl acetate 5:1). The mixture is filtered with Celite (10 g), the filter is washed with chloroform and the solvents are evaporated in vacuo; yield 11.9 g (93%) of (S)-1-fluoro-2-methoxymethoxy-3-(p-touenesulfonyloxy)propane.

For $C_{12}H_{15}FO_5S$ (290.3) calculated: 49.65% C, 5.20% H, 6.54% F, 11.04% S; found: 49.85% C, 5.34% H, 6.40% F, 10.91% S.

A mixture of this product (2.45 g), acetic anhydride (5 ml) and boron trifluoride etherate (1 ml) is stirred at 0° C. for 2 h. Then the reaction mixture is shaken with a mixture of sodium hydrogen carbonate (10 g), water (100 ml) and toluene (100 ml). The aqueous layer is separated, the toluene layer is washed with water (2×50 ml) and dried over magnesium sulfate. Evaporation of the solvent gives (S)-2-acetoxymethoxy-1-fluoro-3-(p-toluenesulfonyloxy)propane in practically quantitative yield. For $C_{13}H_{17}FO_6S$ (320.1) calculated: 48.73% C, 5.35% H, 5.93% F, 10.00% S: found: 48.82% C, 5.51% H, 5.80% F, 9.95% S.

This compound (11.0 g) is codistilled with toluene (3×10 ml), then toluene (20 ml) and bromotrimethylsilane (6.82 ml) are added and the mixture is heated to 80° C. for 16 h. Toluene is distilled off, the residue is codistilled with toluene (3×10 ml) and heated with triisopropyl phosphite (10 ml) at 50° C. for 2 h. The mixture is again codistilled with toluene and the remaining oil is chromatographed on silica gel (100 g) by successive elution with toluene, toluene-ethyl acetate (5:1) and toluene-ethyl acetate (1:1). Yield 11 g of (S)-1-fluoro-2-(diisopropylphosphonylmethoxy)-3-(p-toluenesulfonyloxy)-propane; $[\alpha]_D+12.5°$ (c 0.8, $CHCl_3$). For $C_{17}H_{28}FO_7PS$ (426.4) calculated: 47.87% C, 6.61% H, 4.45% F, 7.26% P, 7.51% S; calculated: 48.04% C, 6.97% H, 4.56% F, 7.45% P, MS, m/e (rel. %): 427 (M+H, 55), 385 (M-iPr, 17), 342 (M-2 iPr, 100), 259 (9), 171 (TsO, 36). $^1$H NMR (DMSO): 1.20 d, 6H ($CH_3$, iPr); 1.26 d, 6H ($CH_3$, iPr); 2.43 s, 3H ($CH_3$, Ts); 3.8–4.8 m, 9H (HCO, $H_2CF$); 7.3–7.8 m, 4H (arom. protons, Ts).

Example 2

Phosphorus pentoxide is added to a stirred mixture of (R)-1-fluoro-3-(p-toluenesulfonyloxy)-2-propanol (11 g, 44.3 mmol), dimethoxymethane (11 ml) and dichloromethane (11 ml) at room temperature until the starting compound disappears in favour of the desired product (monitored by TLC in toluene-ethyl acetate 5:1). Celite (10 g) is added to the reaction mixture which is then filtered and the Celite is washed with chloroform. The solvent is evaporated from the filtrate to afford 11.9 g (93%) of (R)-1-fluoro-2-methoxy-methoxy-3-(p-toluenesulfonyloxy)propane. This product is processed as described in Example 1, yield lag (R)-2-acetoxymethoxy-3-fluoro-1-p-toluenesulfonyloxypropane in quantitative yield. For $C_{13}H_{17}FO_6S$ (320.1) calculated: 48.73% C, 5.35% H, 5.93% F, 10.00% S; found: 48.82% C, 5.51% H, 5.80% F, 9.95% S. The product is processed according to Example 1, giving (R)-1-fluoro-2-(diisopropylphosphonylmethoxy)-3-(p-toluenesulfonyloxy)propane in 75% yield. $[\alpha]_D-12.8°$ (c 0.8, $CHCl_3$). For $C_{17}H_{28}FO_7PS$ (426.4) calculated: 47.87% C, 6.61% H, 4.45% F, 7.51% S; found: 48.13% C, 6.91% H, 4.52% F, 7.35% S. MS, m/e (rel. %): 427 (M+H, 55), 385 (M-iPr, 17), 342 (M-2 iPr, 100), 259, 171 (TsO, 36). $^1$H NMR (DMSO): 1.20 d, 6H (iPr); 1.26 d, 6H (iPr); 2.43 s, 3H ($CH_3$, Ts); 3.8–4.8 m, 9H (HCO, $H_2CF$), 7.3–7.8 m, 4H (atom. proton, Ts).

Example 3

Sodium hydride (60% suspension in paraffin oil, 1.125 g, 28 mmol) is added to a suspension of $N^6$-benzoyladenine (6.5 g, 27 mmol) in dimethylformamide (100 ml) and the mixture is stirred and heated at 60° C. for 15 min. After addition of (S)-1-fluoro-2-(diisopropylphosphonylmethoxy)-3-(p-toluenesulfonyloxy)propane (10 g, 23.6 mmol) the mixture is further stirred and heated at 80° C. for 6 h. The reaction mixture is then neutralized with acetic acid and dimethylformamide is evaporated at 40° C./100 Pa. The residue is extracted with chloroform, the chloroform extracts are filtered through Celite and the filtrate is concentrated in vacuo. The sirupy residue is chromatographed on a column of silica gel (500 g) in a mixture of chloroform and methanol (50:1); yield 3.7 g (32%) of (S)-9-(3-fluoro-2-diisopropylphosphonylmethoxylpropyl)-$N^6$-benzoyladenine. For $C_{22}H_{29}FN_5O_5P$ (493.5) calculated: 53.54% C, 5.92% H, 3.85% F, 14.19% N, 6.27% P; found: 53.71% C, 5.83 H, 3.71% F, 13.97% N.

Sodium hydride (50 mg, 2 mmol) is added to a solution of this compound (2.1 g, 4.25 mmol) in methanol (20 ml). After standing at room temperature for 16 h, acetic acid (250 μl) is added, the mixture is concentrated to a small volume and the residue is chromatographed on a column of silica gel in a mixture of chloroform and methanol (30:1). Yield 1.11 g (67%) of (S)-9-[3-fluoro-2-(diisopropylphosphonylmethoxy)propyl]adenine, m.p. 72°–74° C. (toulene). For $C_{15}H_{25}FN_5O_4P$ (389.4) calculated: 46.26% C, 6.47% H, 4.87% F, 17.98% N, 7.95% P; found: 47.26% C, 7.31% H, 4.90% F, 17.13% N, 7.26% P. MS, m/e (rel. %): 389 (M, 10), 374 (M-$CH_3$, 8), 288 (20), 209 (M-$C_2P(O)(OiPr)_2$, 48), 195 ($OCH_2P(O)(OiPr)_2$, 100), 174 (12), 149 (Ade$CH_2$, 40), 135 (Ade, 60). $^1$H NMR (DMSO): 1.08–1.20 m, 12H ($CH_3$, iPr); 3.7–4.7 m, 9H (HCO, $H_2CF$); 7.19 bs, 2H ($NH_2$); 8.09 s, 1H (H-8, Ade); 8.15 s, 1H (H-2, Ade).

Bromotrimethylsilane (2.17 ml, 16.4 mmol) is added at room temperature to a solution of the above product (1.6 g, 4.1 mmol) in acetonitrile (8 ml) and the mixture is stirred at ambient temperature for 24 h. The reaction mixture is concentrated to a minimum volume, the residue is codistilled 2% with toluene (2×10 ml) and with methanol (10 ml) and aqueous solution of ammonia (10 ml) is added. After standing for 1 h at room temperature, the solution is evaporated to dryness, the residue is dissolved in a minimum amount of water and the solution is applied onto a column of cation-exchanger Dowex 50 ($H^+$-form, 50 ml). The column is washed with water until the eluate exhibits negative reaction to bromides and then the product is eluted from the column with 2% aqueous ammonia. The obtained eluate is concentrated to a minimum volume and applied onto a column of anion-exchanger Dowex 1 (acetate form, 50 ml). The column is washed with water to negative reaction to ammonia and the product is eluted with 1H acetic acid. Evaporation of the solvents and codistillation of the residue with water affords 1.1 g (91%) of (S)-9-(3-fluoro-2-phosphonomethoxypropyl)adenine, m.p.194°–197° C., $[\alpha]_D-16.9$ (c 0.38, water). For $C_9H_{13}FN_5O_4P$ (305.2) calculated: 35.41% C, 4.29% H, 6.22% F, 22.94% N, 10.14% P; found: 35.20% C, 4.43% H, 5.85% F, 22.73% N, 10.44% P.

Example 4

Sodium hydride (60% suspension in paraffin oil, 1.125 g, 28.1 mmol) is added to a suspension of $N^6$-benzoyladenzine (6.5 g, 26.9 mmol) in dimethyl formamide (100 ml) and the stirred mixture is heated at 60° C. for 15 min. After addition of (R)-1-fluoro-2-(diisopropylphosphonylmethoxy)-3-(p-toluenesulfonyloxy)propane (10 g, 23.6 mmol), the mixture is further stirred and heated at 80° C. for 6 h. It is then neutralized with acetic acid and the dimethylformamide is evaporated at 40° C. and 100 Pa. The residue is extracted with chloroform, the combined chloroform extracts are filtered through Celite and the solvent is evaporated in vacuo. The sirupy residue is chromatographed on a column of silica gel (500 g) in a mixture of chloroform and methanol. (50:1), yielding 3.7 g (32%) of (R)-)-(3-fluoro-2-(diisopropylphosphonylmethoxypropyl))-$N^6$-benzoyladenine. For $C_{22}H_{29}FN_5O_5P$ (493.5) calculated: 53.54% C, 5.92% H, 3.85% F, 14.19% N, 6.27% P; found: 53.67% C, 5.99% H, 3.70% F, 13.95% N, 6.40% P.

Sodium hydride (50 mg, 2 mmol) is added to a solution of this product (2.1 g, 4.25 mmol) in methanol. (20 ml). After standing for 16 h at room temperature, acetic acid (250 μl) is added, the mixture is concentrated in vacuo to a minimum volume and chromatographed on a column of silica gel in a mixture of chloroform and methanol (30:1), affording 1.1 g (67%) of (R) -9-[3-fluoro-2- diisopropylphosphonylmethoxypropyl)]adenine, m.p. 72°–74° C. (toluene). For $C_{15}H_{25}FN_5O_4P$ (389.4) calculated: 46.26% C, 6.47% H, 4.87% F, 17.89% N, 7.95% P; found: 47.16% C, 7.12% H, 4.81% F, 17.23% N, 7.46% P. MS, m/e (rel. %): 389 (M, 10), 374 (M-CH$_3$, 8), 288 (20), 209 (M-CH$_2$P(O)(OiPr)$_2$, 48), 195 (OCH$_2$P(O)(OiPr)$_2$, 100), 174 (12), 149 (AdeCH$_2$, 40), 135 (Ade, 60). $^1$H NMR (DMSO): 1.08–1.20 m, 12H (CH$_3$, iPr); 3.7–4.7 m, 9H (HCO, H$_2$CF); 7.19 bs, 2H (NH$_2$); 8.09 s, 1H (H-8, Ade); 8.15 s, 1H (H-2, Ade).

Bromotrimethylsilane (2.17 ml, 16.4 mmol) is added at room temperature to a solution of this compound (1.6 g, 4.1 mmol) in acetonitrile (8 ml) and the mixture is stirred for 24 h at room temperature. The reaction mixture is concentrated in vacuo minimum volume, the residue is codistilled with toluene (2×10 ml) and then with methanol (10 ml) and 2% aqueous ammonia solution (10 ml) is added. After 1 h at room temperature, the solution is evaporated to dryness, the residue is dissolved in a minimum amount of water and the solution is applied onto a column of cation-exchanger Dowex 50 (H$^+$-form, 50 ml). The column washed with water negative reaction to bromides and the product is eluted from the column with 2% aqueous solution of ammonia. The obtained solution is concentrated in vacuo to a minimum volume and the residue is applied onto a column of anion-exchanger Dowex 1 (acetate form, 50 ml). The column is washed with water and the product is eluted with 1M acetic acid. Evaporation in vacuo and codistillation of the residue with water affords (R)-9-(3-fluoro-2-phosphonomethoxypropyl)adenine (1.14 g, 91%), m.p. 194°–197° C., $[\alpha]_D+18.68°$ (c 0.4, water). For $C_9H_{13}FN_5O_4P$ (305.2) calculated: 35.41% C, 4.29% H, 6.22% F, 22.94% N, 10.14% P; found: 36.65% C, 5.34% H, 5.77% F, 20.14% N, 9.79% P.

Example 5

A mixture of 2-amino-6-chloropurine (1.75 g, 10.3 mmol), sodium hydride (60% suspension in paraffin oil, 376 mg, 9.4 mmol) and dimethylformamide (25 ml) is heated at 90° C. for 5 min. (R)-1-Fluoro-2-(diisopropylphosphonylmethoxy)-3-(p-toluene sulfonyloxy)propane (4.0 g, 9.4 mmol) is then added and the mixture is heated under stirring at 90° C. for 2 h (the reaction is monitored by TLC in chloroform-methanol 5:1). The solvent is evaporated at 40° C. and 100 Pa, the residue is mixed with Celite (25 ml) and chloroform (150 ml) and the obtained suspension is filtered through Celite. The filtrate is concentrated to a minimum volume and the residue is chromatographed on a column of silica gel (150 g) in a mixture of chloroform and methanol (50:1 ), affording 2.8 g (68%) of (R)-2-amino-9-(2-diisopropylphosphonylmethoxy-3-fluoropropyl)-6-chloropurine, m.p. 133°–134° C. (toluene). For $C_{15}H_{24}ClFN_5O_5P$ (439.8) calculated: 40.96% C, 5.50% H, 8.06% Cl, 4.32% F, 15.92% N, 7.04% P; found: 41.05% C, 5.53% H, 8.48% Cl, 4.40% F, 15.96% N, 7.20% P. MS, m/e (rel. %): 424 (M, 75), 390 (26), 340 (100), 306 (25), 258 (10), 228 (19), 170 (34), 134 (17), 113 (12).

A mixture of this compound (1 g, 2.27 mmol) and sodium azide (2.0 g) in dimethylformamide (15 ml) is heated at 110° C. for 5 h. The solvent is evaporated in vacuo, the residue is suspended in chloroform, silica gel (4 g) is added and the mixture is evaporated to dryness. This material is applied onto a column of silica gel (20 ml), the product is eluted with a mixture of chloroform and methanol (10:1) and purified by chromatography on a column of silica gel using a mixture of chloroform and methanol (30:1) as eluent. Yield 700 mg (69%) of (R)-2-amino-6-azido-9-(2-diisopropylphosphonylmethoxy-3-fluoropropyl)purine, m.p. 146°–148° C. For $C_{15}H_{24}FN_8O_5P$ (446.36) calculated: 40.35% C, 5.41% H, 4.25% F, 25.10% N, 6.93% P; found: 40.45% C, 5.56% H, 4.01% F, 25.23% N, 6.81% P. MS, m/e (rel. %): 445 (M-H, 1), 431 (100), 405 (21), 390 (3), 319 (9), 225 (8), 210 (9), 150 (11).

A mixture of this compound (150 mg, 0.336 mmol), bromotrimethylsilane (111 μl 0.84 mmol) and acetonitrile (1.8 ml) is stirred at room temperature for 24 h. The reaction mixture is then codistilled with toluene, a dilute aqueous ammonia solution is added (5:1, 5 ml), the solution is concentrated in vacuo, the residue is codistilled with water, dissolved in the same solvent and the solution is applied onto a column of cation-exchanging resin (Dowex 50) in H$^+$-form. The column is washed with water to negative reaction to bromide ions and the compound is then obtained by elution with dilute aqueous ammonia. After evaporation, the product is dissolved in water and applied onto a column of an anion-exchanging resin (e.g. Dowex 1 ) in acetate form. The column is first washed with water and then tile compound is elated with 1M acetic acid. Evaporation of the solvent and codistillation of the residue with water affords 80 mg (69%) of (R)-2-amino-6-azido-9-(3-fluoro-2-phosphonomethoxypropyl)purine. For $C_9H_{12}FN_8O_4P$ (327.2) calculated: 33.03% C, 3.69% H, 34.24% N, 9.46% P; found: 33.14% C, 3.78% H, 34.50% N, 9.30% P.

Example 6

A mixture of (R)-2-amino-9-(2-diisopropylphosphonylmethoxy-3-fluoropropyl)-6-chloropurine (500 mg, 1.14 mmol) according to Example 5 and 75% trifluoroacetic acid (5 ml) is allowed to react at room temperature for 48 h (monitoring by TLC in chloroform-methanol 5:1 ). The reaction mixture is concentrated in vacuo on a rotary evaporator, the residue is codistilled with water, neutralized with a mixture of aqueous ammonia and methanol (1:10, 15 ml) and the solvent is evaporated to dryness. Chromatography on a column of silica gel (Silpearl, 30 ml) in a mixture of chloroform and methanol (20:1) affords 440 mg (92%) of (R)-9-(2-diisopropylphosphonylmethoxy-3-fluoropropyl)guanine, m.p. 165°–173° C. For $C_{15}H_{25}FN_5O_6P$ (421.4) calculated: 42.75% C, 5.98% H, 4.50% F, 16.62% N, 7.35% P; found: 42.95% C, 5.92% H, 4.40% F, 17.16% N, 7.34% P. MS, m/e (rel. %): 420 (M-H, 5), 406 (100), 364, (13), 322 (50), 304 (4), 262 (4), 226 (5), 210 (10), 151 (19).

A mixture of this compound (290 mg, 0.7 mmol), bromotrimethylsilane (364 mg, 2.75 mmol) and acetonitrile (3 ml ) is stirred at room temperature for 24 h. Then the reaction mixture is codistilled with toluene, the residue is mixed with dilute aqueous ammonia (5:1 , 5 ml), the solution is concentrated, codistilled with water and the residue in aqueous solution is applied onto a column of a cation-exchanging resin (Dowex 50) in H+-form. The column is washed with water to negative bromide reaction and the compound is eluted with dilute aqueous ammonia and applied onto a column of an anion-exchanger (Dowex 1) in acetate form. The column is washed with water and the product is eluted with 1M acetic acid. Evaporation of the solvents and codistillation with water affords (R)-9-(3-fluoro-2-phosphonomethoxypropyl)guanine (210 mg, 95%). For $C_9H_{13}FN_5O_5P$ (321.2) calculated: 33.65% C, 4.07% H, 5.91% F, 21.80% N, 9.64% P; found: 33.26% C, 5.09% H, 6.00% F, 21.78% N, 8.47% P. MS, m/e (rel. %): 322 (M+H, 50), 279 (10), 257 (8), 228 (10), 181 (28), 149 (100), 110 (100).

Example 7

A mixture of (R)-2-amino-6-azido-9-(2-diisopropoxyphosphonylmethoxy-3-fluoropropyl)purine (according to Example 5, 300 mg) and 10% palladium on carbon (30 mg) in methanol (6 ml) is stirred at room temperature for 10 h in hydrogen atmosphere. The reaction mixture is filtered and the solvent evaporated. Chromatography on a column of silica gel (30 ml) in a mixture of chloroform and methanol (40:1) gave 217 mg (77%) of (R)-2,6 -diamino-9 -( 2-diisopropylphosphonylmethoxy-3-fluoropropyl)purine. For $C_{15}H_{26}FN_6O_4P$ (404.4) calculated: 44.55% C, 6.48% H, 4.70% F, 20.78% N, 7.66% P; found: 44.35% C, 6.67% H, 4.61% F, 20.53% N, 7.52% P.

To a suspension of this compound (150 mg, 0.37 mmol) in acetonitrile (1.5 ml) is added bromotrimethylsilane (263 μl, 2.0 mmol) and the mixture is stirred at room temperature for 24 h. Then the reaction mixture is codistilled with toluene and dilute aqueous ammonia (10:1, 5 ml) is added. The solution is concentrated, the residue codistilled with water and in aqueous solution applied onto a column of a cation-exchanging resin (Dowex 50) in H+-form. The column is washed with water to negative bromide reaction, the product is eluted with dilute aqueous ammonia and applied onto a column of an anion-exchanger (Dowex 1 ) in acetate form. The column is washed with water and the product is then eluted with 1M acetic acid. Evaporation of solvents followed by codistillation with water affords 50 mg of (R)-2,6-diamino-9-(3-fluoro-2-phosphonomethoxypropyl)purine. For $C_9H_{14}FN_6O_4P$ (320.2) calculated: 33.76% C, 4.41% H, 5.93% F, 26.24% N, 9.67% P; found: 33.46% C, $0.83% H, 5.33% F, 26.04% N, 9.37% P.

Example 8

A mixture of (R)-2-amino-9-(2-diisopropylphosphonylmethoxy-3-fluoropropyl) -6-chloropurine (according to Example 5, 500 mg, 1.14 mmol) and 10% palladium on carbon (50 mg) in methanol (10 ml) is stirred at room temperature in hydrogen atmosphere for 4 h. The reaction is monitored by TLC (chloroform-methanol 5:1). The reaction mixture is neutralized with a mixture of concentrated aqueous ammonia and methanol (1:10, 10 ml), filtered and evaporated. Chromatography on a column of silica gel (50 ml) successively in 50:1 and 20:1 mixtures of chloroform and methanol affords 200 mg (45%) of (R)-2-amino-9-(2-diisopropylphosphonylmethoxy-3-fluoropropyl)purine. For $C_{15}H_{25}FN_5O_4P$ (389.4) calculated: 46.27% C, 6.47% H, 4.88% F, 17.99% N, 7.95% P; found: 44.71% C, 6.44% H, 4.30 %F, 17.44% N, 8.14% P.

To a solution of this compound (80 mg, 0.21 mmol) in acetonitrile (1.6 ml) is added bromotrimethylsilane (280 μl, 2.1 mmol) and the mixture is stirred at room temperature for 24 h. After evaporation in vacuo, the residue is codistilled with toluene, a dilute aqueous solution of ammonia (1:10, 5 ml) is added, the solution is concentrated and the residue codistilled with water. An aqueous solution of the residue is applied onto a column of a cation-exchanger (Dowex 50) in H+-form. The column is washed with water to negative bromide reaction and then with aqueous ammonia. The residue after evaporation of the ammonia eluate is applied onto a column of an anion-exchanger (Dowex 1) in acetate form, the column is washed with water and the product is eluted with 1M acetate acid. Evaporation of the solvents and codistillation with water affords 50 mg (80%) of (R)-1-amino-9-(3-fluoro-2-phosphonomethoxypropyl)purine. For $C_9H_{13}FN_5O_4P$ (305.2) calculated: 35.41% C, 4.29% H, 6.22% F, 22.94% N, 10.14% P; found: 35.59% C, 4.40% H, 6.40% F, 23.15% N, 10.30% P.

We claim:

1. Compounds of the general formula VIII

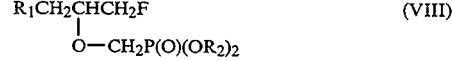

where $R_1$ is a reactive chloro, p-toluenesulfonyloxy or methanesulfonyloxy group, $R_2$ is alkyl, and the absolute configuration at carbon atom C2 is R, S or RS.

2. The compounds of claim 1 wherein $R_2$ is isopropyl.

3. The compounds of claim 1 wherein $R_1$ is p-toluenesulfonyl.

4. The method of claim 1 wherein the compound is the (R) enantiomer.

5. A method for using compounds of the general formula VIII to prepare derivatives of heterocyclic purine and pyrimidine bases of the formula VI

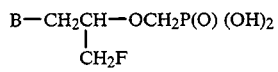   (VI)

where the absolute configuration at carbon atom C2 is R, S or RS and B is a substituted purin-9-yl, purin-7-yl, pyrimidin-1-yl or pyrimidine-3-yl moiety or their aza or diaza analogues, comprising reacting compounds of formula VIII

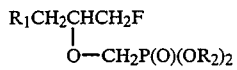   (VIII)

where $R_1$ is a reactive chloro, p-toluenesulfonyloxy or methanesulfonyloxy group, $R_2$ is alkyl and the absolute configuration at carbon atom C2 is R, S or RS with a sodium salt of the substituted purine or pyrimidine heterocyclic base, its aza or diaza analogue, or their acyl derivatives, with an alkali metal carbonate, treating the residue with sodium ethoxide in methanol and then with bromotrimethylsilane in an inert organic solvent, and isolating the resulting compounds of formula VI by chromatography.

6. The method of claim 5 wherein B is a purin-9-yl base selected from the group consisting of adenine, 2,6-diaminopurine, 6-methylthiopurine, 3-deazaadenine, hypoxanthine, guanine, 2-aminopurine, 1-deazaadenine, 2-hydroxyadenine, 2-amino-6-chloropurine, 2-amino-6-azidopurine, and $N^6$-benzoyladenine.

7. The method of using compounds of the formula II comprising reacting 1-fluoro-2,3-propanediols of the general formula II.

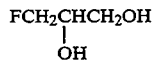   (II)

where the absolute configuration at carbon atom C2 is R, S or RS,
  with p-toluenesulfonyl chloride in the presence of a tertiary amine in an inert organic solvent, whereby are obtained 1-fluoro-3-p-toluenesulfonyloxy-2-propanols of the general formula III

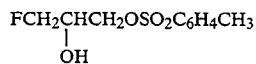   (III)

where the absolute configuration at carbon atom C2 is R, S or RS,
  reacting compound of formula III with dimethoxymethane in the presence of phosphorus pentoxide in an inert organic solvent whereby are obtained the resulting 1-fluoro-2-methoxymethoxy-3-p-toluenesulfonyloxypropanes of the formula IV

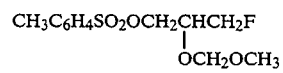   (IV)

where the absolute configuration at carbon atom C2 is R, S or RS,
  treating the compounds of Formula IV with acetic anhydride in the presence of a Lewis acid whereby are obtained 2-acetoxymethoxy-1-fluoro-3-p-toluenesulfonyl-oxypropanes of the formula V

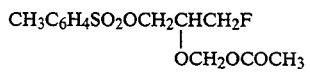   (V)

where the absolute configuration at carbon atom C2 is R, S or RS,
  heating the compounds of formula V with bromotrimethylsilane evaporating the volatile material in vacuo and reacting the residue with trialkyl phosphite, and isolating the compounds of the formula IX

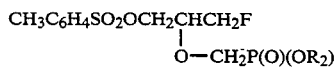   (IX)

wherein $R_2$ is alkyl and the absolute configuration at carbon atom C2 is R, S or RS.

* * * * *